United States Patent

Hermosillo-Valadez et al.

[11] Patent Number: 5,880,843
[45] Date of Patent: Mar. 9, 1999

[54] APPARATUS AND METHOD FOR DETERMINING THE OPTICAL DISTORTION OF A TRANSPARENT SUBSTRATE

[75] Inventors: Gerardo Hermosillo-Valadez, Estado de México; Daniel Jimenez Farias, León; Alejandra Ramirez-Ortiz, Durango; Nancy Gutierrez-Garza, Nuevo León, all of Mexico

[73] Assignee: Vitro Flotado, S.A. de C.V., Nuevo Leon, Mexico

[21] Appl. No.: 922,660

[22] Filed: Sep. 3, 1997

[51] Int. Cl.⁶ ................................... G01B 11/30
[52] U.S. Cl. .................. 356/371; 356/124; 356/445; 356/429
[58] Field of Search .................. 356/124, 125–127, 356/371, 239, 445–446, 429–430; 250/359.01, 359.05, 359.07, 359.08; 382/141; 348/88

[56] References Cited

U.S. PATENT DOCUMENTS

| 3,788,750 | 1/1974 | Maltby | 356/239 |
|---|---|---|---|
| 3,792,930 | 2/1974 | Obenreder | 356/239 |
| 3,857,637 | 12/1974 | Obenreder | 356/237 |
| 4,272,190 | 6/1981 | Shapiro | 356/124 |
| 4,453,827 | 6/1984 | Taboada | 356/127 |
| 4,585,343 | 4/1986 | Schave et al. | 356/237 |
| 4,645,337 | 2/1987 | Obenreder | 356/239 |
| 5,206,700 | 4/1993 | Reynolds et al. | 356/237 |
| 5,210,592 | 5/1993 | Bretschneider | 356/371 |
| 5,251,010 | 10/1993 | Maltby, Jr. | 356/239 |
| 5,724,140 | 3/1998 | Haywood | 356/239 |
| 5,726,749 | 3/1998 | Schave | 356/239 |

Primary Examiner—Robert Kim
Attorney, Agent, or Firm—Abelman, Frayne & Schwab

[57] ABSTRACT

An apparatus and a method for determining the reflected optical power and the transmitted optical power of a transparent plate, for example the distortion transmitted and the distortion reflected from the surfaces of a glass plate by digital analysis of images in real time. The apparatus including a light source mounted to send a light beam toward a glass plate, at an acute incidence angle regarding the normal of the plate causing in this way a second light beam reflected by the first surface and a third light beam reflected by the second surface of the glass. These reflected beams are directed toward a mirror of first surface which directs the reflected beams toward a light integrating screen and toward a zoom lens to be afterwards directed to a video camera. The optical distortion of the glass plate is determined by measuring the changes of the separation of the reflected beams using the technique of real-time digital image analysis

12 Claims, 4 Drawing Sheets

$\theta_1 = \theta_2 \neq \theta_3$

APPARATUS AND METHOD FOR DETERMINING THE OPTICAL DISTORTION OF A TRANSPARENT SUBSTRATE

BACKGROUND OF THE INVENTION

A. Field of the Invention

This invention is related to an apparatus and a method for determining the optical distortion of a transparent substrate, such as a float glass sheet, as a function of the changes in the separation of two coherent light beams reflected by the surfaces of the glass sheet, by means of a methodology of real time digital image analysis.

B. Description of the Related Art

In the manufacture of transparent sheets or plates, such as in the manufacture of glass sheets by the floating process, the drawing process or other processes, some defects may appear in the resulting glass sheets.

The optical distortion of the glass sheet is among the above mentioned defects. One type of optical distortion is the distortion of the glass surfaces which produces a distorted reflection of an image such as, for example, convex portions of the glass surface produce a shrinkage of the reflected image while concave portions produce a magnifying of the image.

Another kind of distortion is the transmitted distortion which produces a distortion of the image when it is seen through the glass.

In U.S. Pat. No. 3,788,750 of Maltby et al, issued on Jan. 29, 1974, the optical distortion, or else the optical quality of the glass, is measured regarding the power of the focal length of a lens measured in diopters which are defined as the unit over the focal length expressed in meters.

In the U.S. Pat. No. 5,210,592 of Bretschneider, issued on May 11, 1993, the optical quality is determined as the optical power defined as the shunt of the angle observed, for example the angle of reflection or the angle of transmission after a location. The greater the local curvature of the surface of the glass, the greater will be the optical power.

A method for describing the distortion of a surface of a glass piece is disclosed in the U.S. Pat. No. 3,857,637 of Obenreder, issued on Dec. 31, 1974. This patent also discloses an apparatus for determining the optical power reflected on an upper surface of a glass piece, which requires, in some cases, a light absorbent material, for example a black painting in optical contact with the lower surface of the glass piece to prevent any reflection of the light beam by this surface. This is for glass sheets of a thickness less than 3/32 of an inch and an incidence angle of 30°. For thickness greater than 3/32 of an inch, a "shell" provided by the apparatus can be suitably used. It is well known that this optical power can be measured for both surfaces if the glass piece is turned down and measured again from the rear surface, but the distortion of both surfaces of the glass sheet cannot be determined in a single operation.

U.S. Pat. No. 4,585,343 of Schave et al, issued Apr. 26, 1986, discloses an apparatus for detecting the distortion of a surface; the apparatus includes a source of light mounted to direct a first light beam toward a surface of the glass sheet at an oblique incidence angle to cause a second light beam when it is reflected by said surface; a light detector mechanism is mounted to receive the reflected light beam which is sensitive to a light pattern on the detector mechanism, produced from the reflected light beam generating an output signal representing the width of the light of said pattern. In this case, the width of the light of the pattern is a function of the surface distortion of the portion of the surface from which the light beam is reflected. While the apparatus is capable of determining the distortion of the surface, this does not represent said distortion in terms of optical power.

The U.S. Pat. No. 5,210,592 of Bretschneider discloses an apparatus in which two parallel light beams having a reciprocal space are directed toward a plate under an acute angle regarding the normal of the plate, the light beams reflected by said plate are received separately by a detector mechanism with a photosensor device and the direction of the light beams reflected is evaluated, in which the four light beams reflected by the two surfaces of the plate over the detector sensitive to the position are necessary to evaluate the parameters for the quantitative determination of the optical quality of the plate. The apparatus is well accepted in terms of the determination of the optical power.

In the present invention it is disclosed that, in order to determine the optical power of a transparent plate, the use of mechanisms for the separation of the light beams, as it is done in the apparatus of the patent of Bretchneider, is not necessary and that the four reflected light beams are not required, but just two of them are enough to determine the optical power by means of the introduction of technique of real-time digital image analysis. This change involves mechanisms different from those disclosed by Bretschneider.

The apparatus of the present invention includes a light source mounted to direct a first light beam toward a surface of the plate at an incidence angle, based on the normal, between 44° and 54°, preferably of about 49°, to cause a second light beam which is reflected specularly to the upper surface of the plate, and a third light beam reflected from the lower surface thereof. The separating space between the light beams is a function of the incidence angle, of the refraction index of the material and of the thickness thereof.

A device is provided for the integration of the reflected light beams, by means of a rotary screen of a diffuse material to obtain two perfectly defined spots from the light beams. Devices are provided for sensing the relative position of the light beams specularly reflected from the surfaces when the plate is moved along a predetermined path with known speed. Calculation means, based on the technique of the real-time image digital analysis, are used to measure the separation of the light beams and computer calculation means are also provided for the determination of the distortion in terms of the optical power, whose internationally-recognized measure unit is the diopter.

As the light beam is swept along the plate, the separation space of the reflected light beams changes in an inverse proportion to the focal distance of the lenses which are formed in the glass (concave or convex). By calculation means involving the use of the real-time digital image analysis technique, the determination of the superficial and transmitting optical distortion is carried out.

A resulting output graphic is provided wherein the longitudinal axis represents the position along the sample, while the vertical axis represents the optical power of the glass. The extent of the curves is proportional to the optical power of the glass, consequently the graphic indicates the distortion in terms of the optical power in any point along the length of the glass sample.

As can be observed, the light source can be displaced in a relative way to the material, or the material and the light source can be moved in turn one in relation to the other.

SUMMARY OF THE INVENTION

It is therefore a main object of the present invention, to provide an apparatus for measuring the optical distortion of a transparent substrate, such as a glass sheet, for determining both the surface distortion and the transmission distortion of said substrate.

It is also a main object of the present invention, to provide an apparatus for measuring the optical distortion of a transparent substrate, of the above disclosed nature, which automatically measures the optical distortion, in terms of the optical power, of said transparent substrate, and particularly a glass plate produced by the floating process, by means of a method consistent enough to use said apparatus as a standard measuring system.

It is still a main objective of the present invention, to provide an apparatus for measuring the optical distortion of a transparent substrate, of the above disclosed nature, comprising a light source directing a first light beam toward a surface of the substrate at an incidence angle between 44° and 54°, to cause a second and third light beams which are reflected specularly to the upper and lower surfaces of the substrate, a rotary screen of a diffuse material to obtain two perfectly defined spots from the light beams, devices for sensing the relative position of the light beams reflected from the surfaces when the plate is moved along a predetermined path with known speed, a calculation device, based on the technique of the real-time image digital analysis, to measure the separation of the light beams and a computer for the determination of the distortion in terms of the optical power.

It is another main objective of the present invention, to provide a method for measuring the optical distortion of a transparent substrate, in one measuring step.

It is also a main objective of the present invention, to provide a method for measuring the optical distortion of a transparent substrate, by directing a light beam toward a substrate of transparent material which reflects a pair of reflected light beams from the upper and lower surfaces of the substrate, directing the reflected light beams toward a light integration device to transform them into two spots of defined light, which are captured and recorded in size and position forming a digital image by means of a video card, which finally are and processed by means of a data processor unit, in order to measure the position of the reflected beams and determining the distortion in terms of optical power.

These and other objects and advantages of the present invention will be apparent to those persons skilled in the art, from the teachings of following detailed description of the invention.

DETAILED DESCRIPTION OF THE INVENTION

The specific embodiments of the apparatus and method for determining the optical distortion of a transparent substrate, in accordance with the present invention, will be now described in combination with the enclosed drawings wherein the same numbers refer to the same components in the shown drawings.

Figure 1:
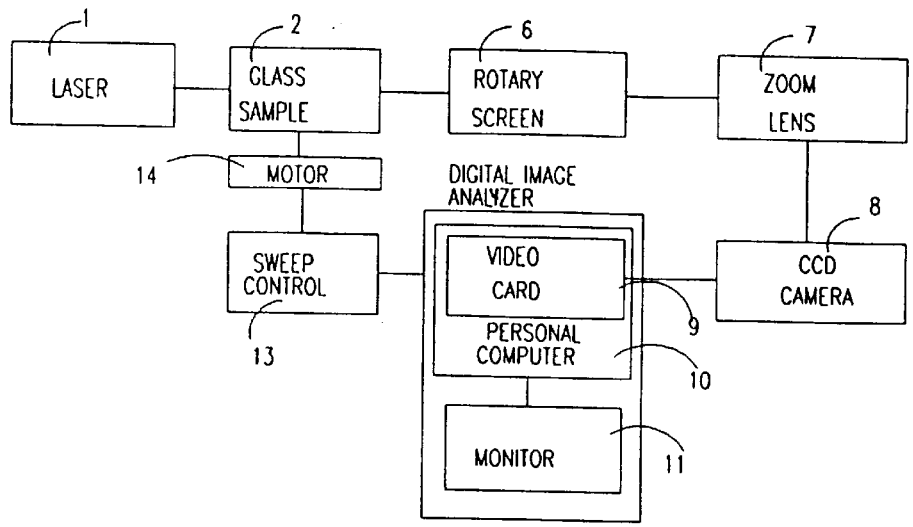
FIG. 1 is a block diagram of the basic components and interrelation thereof, of the apparatus for measuring the optical distortion of a transparent substrate, of the present invention.
Figure 2:
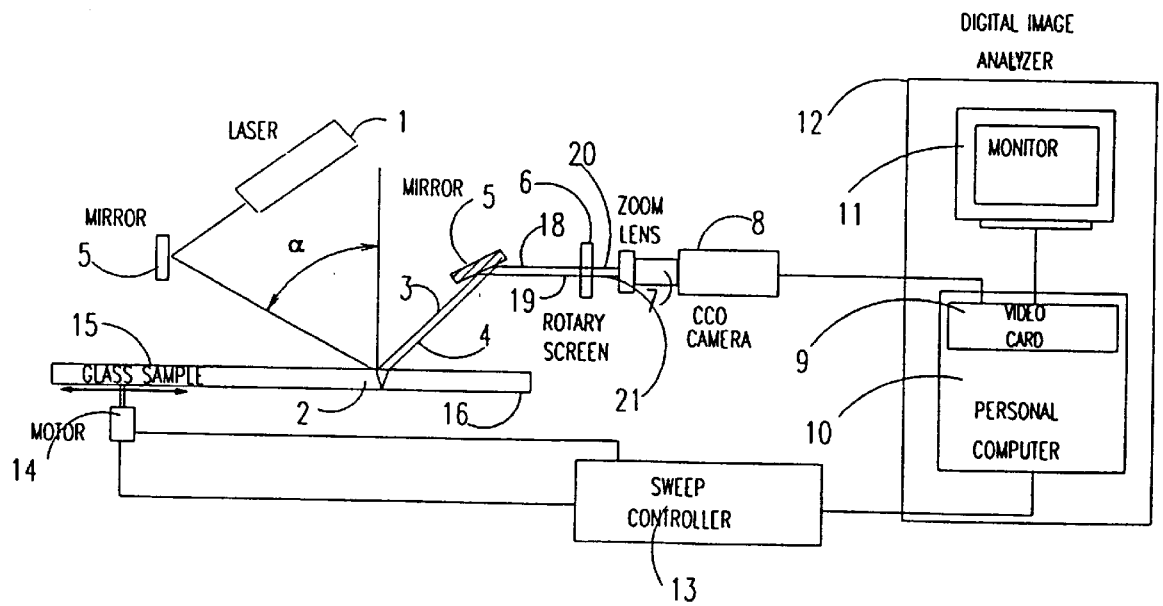
FIG. 2, is a schematic view of the components of the apparatus illustrated in FIG. 1, wherein an action of the measurement over a glass plate is being carrying out.

Referring initially to the apparatus for determining the optical distortion of a transparent substrate, such as a glass sheet produced by the so called "floating process", as shown in FIGS. 1 and 2, which comprises:

a light source1, such as an apparatus providing a laser beam, mounted over the glass sheet, to provide a first light beam LB1 a mirror 5 of first surface, which receives said beam LB and projects it at an incidence angle within 44° and 54°, preferably of 49°, regarding the normal, directing said beam toward a plate of transparent material, for example a glass sheet 2 produced by the floating process, causing a second light beam 3 which is specularly reflected from the upper surface 15 of the glass sheet 2 and a third light beam 4 reflected from the lower surface 16 of the glass sheet 2;

a mirror 5' receives the reflected light beams 3 and 4 and projects them as two horizontal light beams 18, 19 to be processed;

a light integration device, such as a rotary white screen 6, which receives and integrates said light beams 18, 19, to obtain two perfectly defined light spots 20, 21;

a video camera CCD 8 having a zoom lens 7 placed at a determined focal distance form the screen 6, which receives the light spots 20, 21 to be captured and recorded as an image from the light beams in size and position; and a digital image analyzer 12 comprising a video card 9 in order to receive and translate the image of the light spots as a digital image, and a data processor unit, such as a personal computer 10 receiving and processing the digital image of the light stains 20, 21 to measure the separation between them and the relative position of the reflected light beams and determine the distortion in terms of the optical power.

The digital image analyzer system 12 also has a monitor 11 to show the proper position of the reflected and integrated beam spots 20, 21 detected by the video camera.

Also referring to FIGS. 1 and 2, a sweep control mechanism 13, carried out by a control card, automatically keeps the uniform sweeping displacement over the plate, said displacement is physically carried out by a cc synchronic motor 14 which moves the plate 2 by suitable movement transmission means.

Regarding to the method for determining the optical distortion of a transparent substrate, this can be described as comprising:

directing a coherent light beam LB toward a plate of transparent material, such a glass sheet 2 in order to reflect a second light beam 3 which is specularly reflected from the upper surface 15 of the glass sheet 2 and a third light beam 4 reflected from the lower surface 16 of the glass sheet 2;

directing the reflected light beams 2 and 3 toward a light integration device comprising such as a rotary white screen 6, which integrates the light of the two beams 2 and 3 to transform them in two perfectly defined light spots 18 and 19;

capturing the two light spots 18 and 19 by means of a video camera CCD 8 having a zoom lens 7 placed at a determined focal distance from the screen 6, which receives the light stains 20, 21 to be captured and recorded as an image from the light beams in size and position;

receiving and translating the image of the light spots 18 and 19 as a digital image, by means of a digital image analyzer 12 comprising a video card 9; and receiving and processing the digital image of the light spots 20, 21 by means of a data processor unit, such as a personal computer 10, to measure the separation between them and the relative position of the reflected light beams and determine the distortion in terms of the optical power.

The calculation methodology is based on the digital image analysis by means of devices such as a light integrating mechanism, for example a rotary white screen 6 that integrates the beams 3 and 4 specularly reflected from the plate of transparent material 2, into beams 20, 21 of perfectly defined dimensions without components of disperse light; a zoom lens, for example a video zoom 7 with a focal length between 18 and 108 mm. makes the focus for the sensor of the coherent light beams previously integrated by the rotary screen; the focal length determines the sensibility range of the instrument.

At a minimum focal length corresponds a lower sensibility, while at a maximum focal length corresponds the greater sensibility of the instrument which is the maximum capacity to perceive a lower variation in milidopters.

A video camera CCD 8, as for example a SONY XC-75 monochromatic camera, is the sensor mechanism that places the spots of the integrated beams, in size and form, into image elements of 768 horizontal points and 494 vertical points; a digital card as for example the "Data Translation" DT2851, digitizes the information taken by the video camera, into a data matrix of 512×512 pixels equivalent to an angle of 0.003° to carry out the calculation in base of the real-time digital data analysis and sends it in turn to the monitor which acts as an optic support for the position of beams registered by the camera in a position central to the path.

Figure 3:
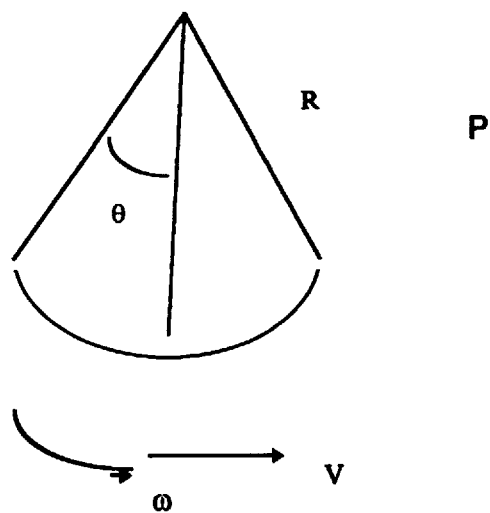
FIG. 3 is a diagram of the optical principle of calculation of the optical power for a moving sample at a constant linear velocity.

The method of calculation using the real-time digital image analysis is based on calculating the central position of the integrated beams and then calculating the separation thereof in real time, all of which allows its calculation according to the definition of the optical power, in accordance with the following equation taken in combination with FIG. 3:

$$P = \frac{1}{R} = \frac{\phi}{V} = \frac{d\theta}{dt} \quad \frac{dt}{dx} = \frac{d\theta}{dx}$$

Wherein dx is in meters and dθ is in radians.

Figure 4:
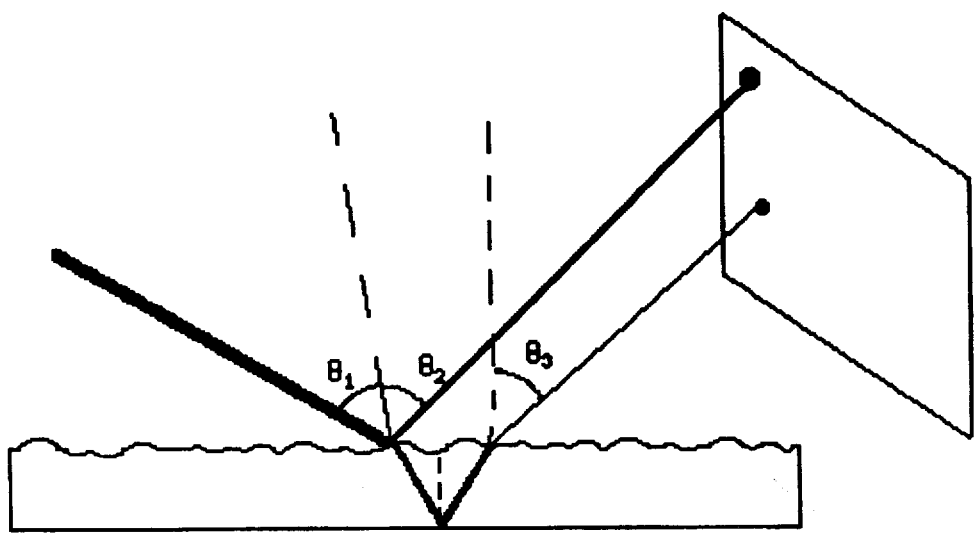
FIG. 4, is a diagram of a possible distortion case of the upper surface of a plate of transparent material such as a glass sheet.
Figure 5:
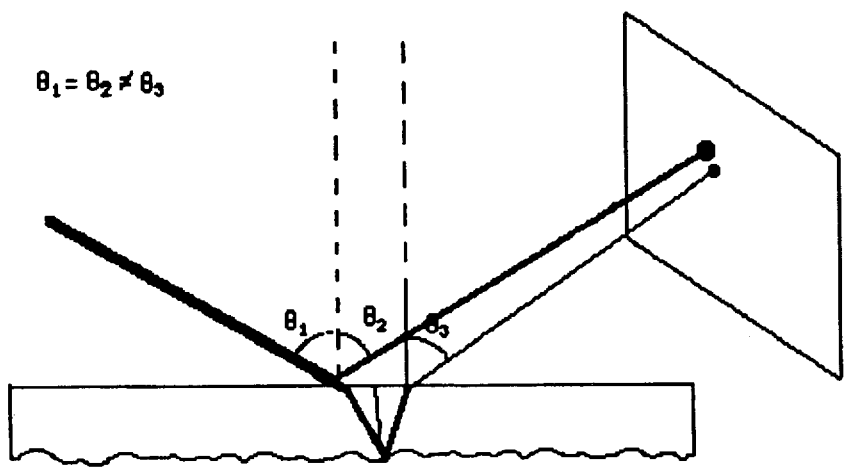
FIG. 5 is a diagram of a possible distortion case of the lower surface of a plate of transparent material such as a glass sheet.
Figure 7A:
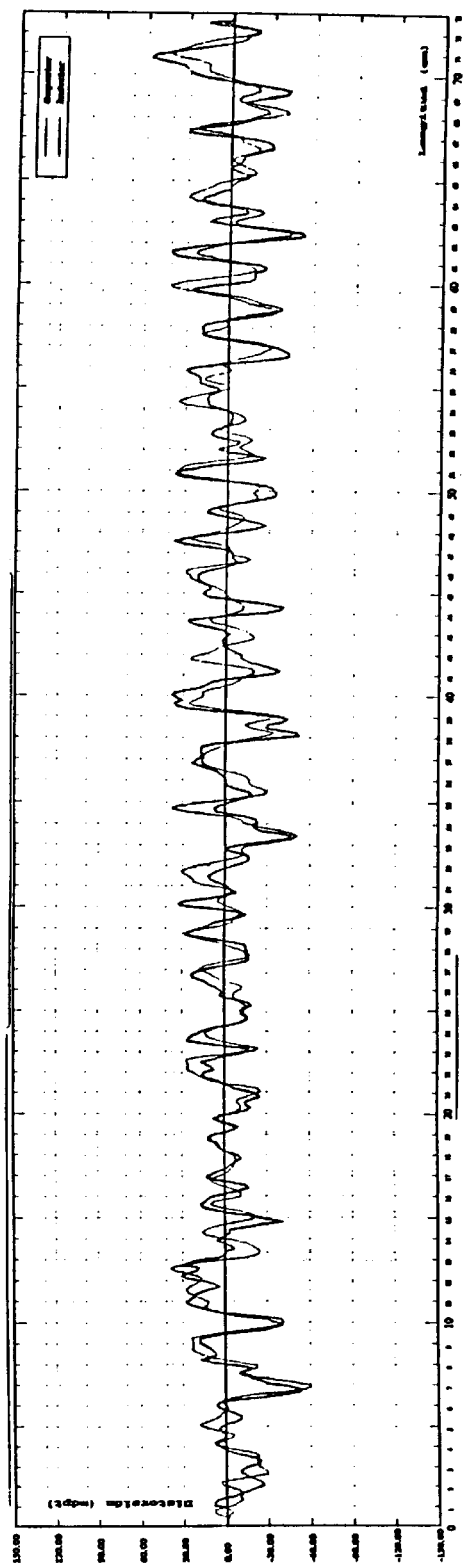
FIGS. 7A and 7B, are graphics representing the behavior of the distortion of both surfaces of an end of the glass sheet obtained by the floating process and of the behavior of the distortion at the transmission, of the same glass sheet.
Figure 7B:
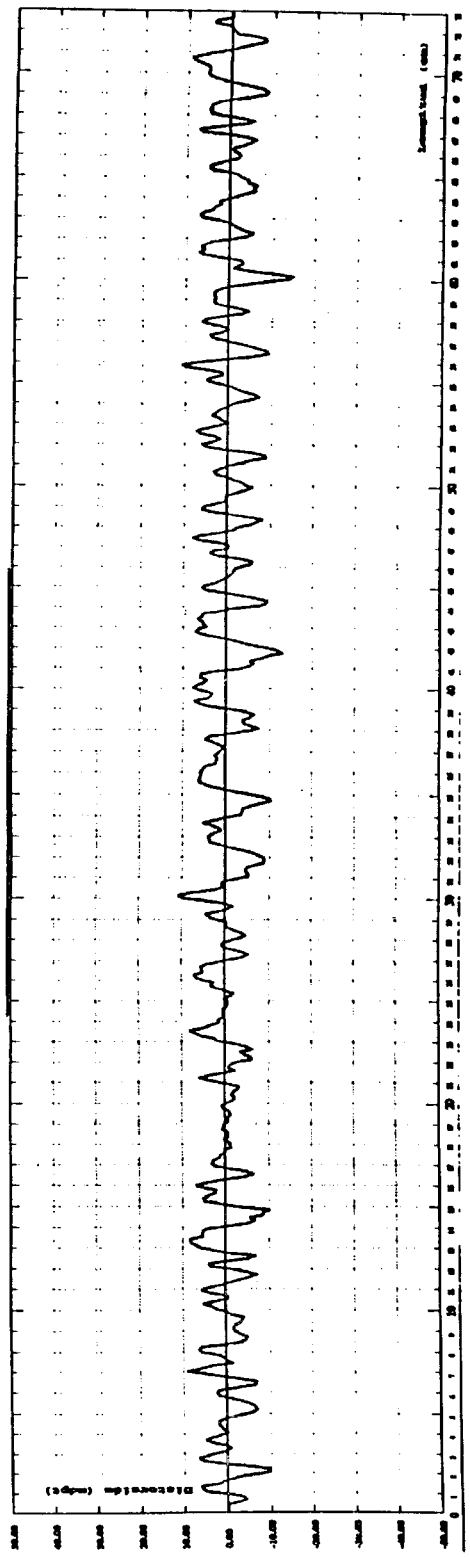

FIG. 4 represents a possible case of the effect of the distortion caused by the upper surface of a plate of transparent material, while FIG. 5 represents a possible case of distortion caused by the lower surface of the plate.

In both cases, a single incident beam and two reflected beams projected on the screen, show the effect of the separation of the beams wherein the beam specularly reflected by the upper surface is of much greater intensity than that of the lower surface, in both cases.

Figure 6:
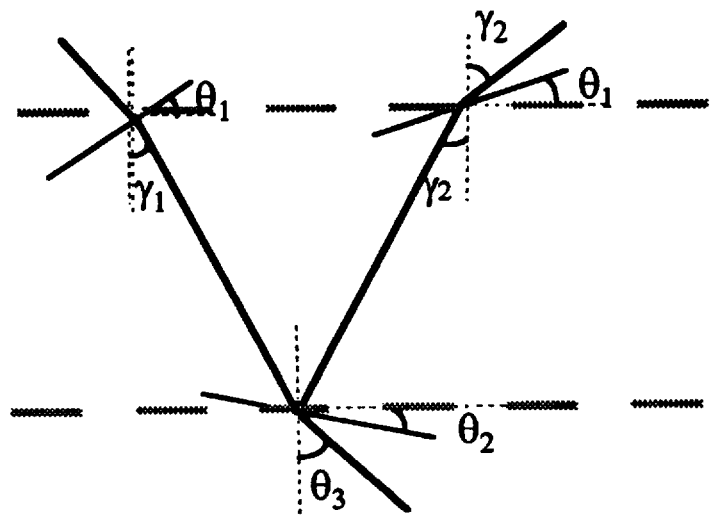
FIG. 6 is a schematic view of the measuring principle applied to a plate of transparent material, as a measure of the refraction and reflection angles of the material.

The calculation of the optical power as a function of the digitalization of the images in real time is given by the following equations based on FIG. 6:

Optical power at the reflection of the upper surface:

$$\theta_1 = \gamma_2 * f_1$$

Optical power at the reflection of the lower surface $$\theta_2 = \frac{-(\gamma_2 + \gamma_1)}{2} * f_2$$

Optical power at the transmission $$\theta_3 = \frac{(\gamma_2 - \gamma_1)}{2} * f_3$$

Wherein $\gamma_1, \gamma_2$: are expressed in pixels $f_1, f_2$ y $f_3$: are gauge factors expressed in radians/pixels.

We claim:

1. An apparatus for determining the optical distortion of a transparent substrate, comprising:

light emitting means mounted on support means spaced over the substrate, to direct a first light beam toward a surface of the substrate, to cause a second light beam which is reflected from the upper surface of the substrate and a third light beam reflected from the lower surface of the substrate;

integrator means receiving the second and third reflected light beams for the integration thereof in order to obtain two perfectly defined spots of the reflected light beams;

sensor means associated with the integrator means, to detect the angle of the light beams reflected from the surfaces of the substrate; and data processor means receiving and processing the spots of the light beams, to measure the position, in the image of the reflected light beams and determining the distortion in terms of optical power.

2. The apparatus according to claim 1, wherein the light emitting means is a solid state laser apparatus which directs the light beam toward a mirror of first surface which projects it toward the substrate at a defined angle between 44° and 54°.

3. The apparatus according to claim 1, wherein the incidence angle regarding the normal of the substrate is of about 49°.

4. The apparatus according to claim 1, wherein the integrator means comprises a rotary screen of a diffuse material and a video camera having a zoom lens receiving the reflected light beams as spots for the integration thereof.

5. The apparatus according to claim 4, wherein the integrator means comprises a mirror receiving the reflected light beams and projects them toward the rotary screen of diffuse material and from this to the video camera having the zoom lens receiving the spots of the reflected beams for the integration thereof, and a video card for transforming the signals of the video camera into digital signals; and a monitor to show and provide information to the data processor means.

6. The apparatus according to claim 1, wherein the data processor means digitally analyzes the images in real time in order to measure the separation between the beams.

7. The apparatus according to claim 1, wherein the data processor means is a personal computer.

8. The apparatus according to claim 4, wherein the data processor means comprises a monitor to show the position of the spots of the reflected and integrated beams detected by the video camera.

9. The apparatus according to claim 1, comprising a movable means for moving the substrate along a determined path and known speed, for the detection of the position of the light beams reflected from the surfaces of the substrate, at the sensor.

10. The apparatus according to claim 9, wherein the movable means comprises a motor for imparting a displacement movement to the substrate and a sweep controller associated with the motor and with the data processor means to detect the position of the light beams reflected from the surfaces of the substrate, at the sensor.

11. The apparatus according to claim 1, wherein the optical power is measured in diopters.

12. A method for determining the optical distortion of a transparent substrate, comprising:

directing a light beam toward a substrate of transparent material which reflects a pair of reflected light beams corresponding to the components of the upper and lower surfaces of the substrate;

directing the reflected light beams toward a light integration device which integrates the light of said beams to transform them into two spots of defined light;

capturing the two light spots by a zoom lens placed at a predetermined focal distance;

receiving the light spots captured by the zoom lens and recording the image of the beams in size and position forming a digital image by means of a video card; and receiving and processing the digital image by means of a data processor unit, in order to measure the position, at the sensor, of the reflected beams and determining the distortion in terms of optical power.

* * * * *